US008535620B2

(12) United States Patent
Takagi

(10) Patent No.: US 8,535,620 B2
(45) Date of Patent: Sep. 17, 2013

(54) METHOD OF FILLING LIQUID SAMPLE

(75) Inventor: Fumio Takagi, Chino (JP)

(73) Assignee: Seiko Epson Corporation (JP)

( * ) Notice: Subject to any disclaimer, the term of this patent is extended or adjusted under 35 U.S.C. 154(b) by 263 days.

(21) Appl. No.: 12/963,684

(22) Filed: Dec. 9, 2010

(65) Prior Publication Data

US 2011/0139294 A1 Jun. 16, 2011

(30) Foreign Application Priority Data

Dec. 14, 2009 (JP) ................................. 2009-282931

(51) Int. Cl.

| | |
|---|---|
| ***B01L 3/00*** | (2006.01) |
| ***G01N 35/00*** | (2006.01) |
| ***G01N 1/10*** | (2006.01) |
| ***C12M 1/36*** | (2006.01) |
| ***C12M 1/22*** | (2006.01) |

(52) U.S. Cl.

USPC .......... 422/500; 436/43; 436/180; 435/288.4; 435/305.2

(58) Field of Classification Search

USPC .................... 422/500; 137/383, 384, 599.01, 137/614.01, 614.02, 861

See application file for complete search history.

(56) References Cited

U.S. PATENT DOCUMENTS 3,986,534 A * 10/1976 Schmidt ............................ 141/1
6,277,642 B1 * 8/2001 Mentzen et al. ................ 436/54
6,287,850 B1 * 9/2001 Besemer et al. ........... 435/287.2
6,803,205 B2 * 10/2004 Duffy et al. ..................... 435/15
7,169,602 B2 * 1/2007 Sandell ...................... 435/288.4
7,214,348 B2 * 5/2007 Desmond et al. ............. 422/502
7,517,498 B2 * 4/2009 Fredrick ....................... 422/560
2002/0125139 A1 * 9/2002 Chow et al. ................... 204/601
2003/0064507 A1 * 4/2003 Gallagher et al. ......... 435/287.2
2005/0042768 A1 * 2/2005 Fredrick ....................... 436/174
2009/0111192 A1 * 4/2009 Kitazawa et al. ............. 436/172
2009/0148912 A1 6/2009 Takagi

FOREIGN PATENT DOCUMENTS

JP 2004-251638 A 9/2004
JP 2006-509199 3/2006
JP 2009-136220 6/2009
WO WO2004-050248 6/2004

* cited by examiner

*Primary Examiner* — Jill Warden
*Assistant Examiner* — Brittany Fisher
(74) *Attorney, Agent, or Firm* — Harness, Dickey & Pierce, P.L.C.

(57) ABSTRACT

A method of filling a liquid sample includes: supplying the liquid sample to a first well of a biochip; adhering a cover and the substrate of the biochip in a loop-shaped area surrounding the first well and plural second wells on the substrate; moving the liquid sample from the first well to the second wells through a space between the cover and the substrate by rotating the biochip around a rotation axis in a state in which the biochip is arranged such that a distance from any one of the second wells to the rotation axis in a vertical direction with respect to the rotation axis is longer than a distance from the first well to the rotation axis in the vertical direction with respect to the rotation axis; and sealing the first well and the second wells by adhering the cover to the substrate to thereby seal.

5 Claims, 6 Drawing Sheets

FIG.12
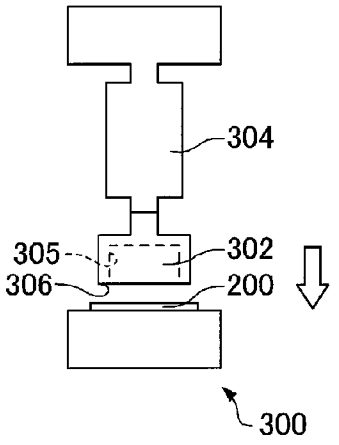
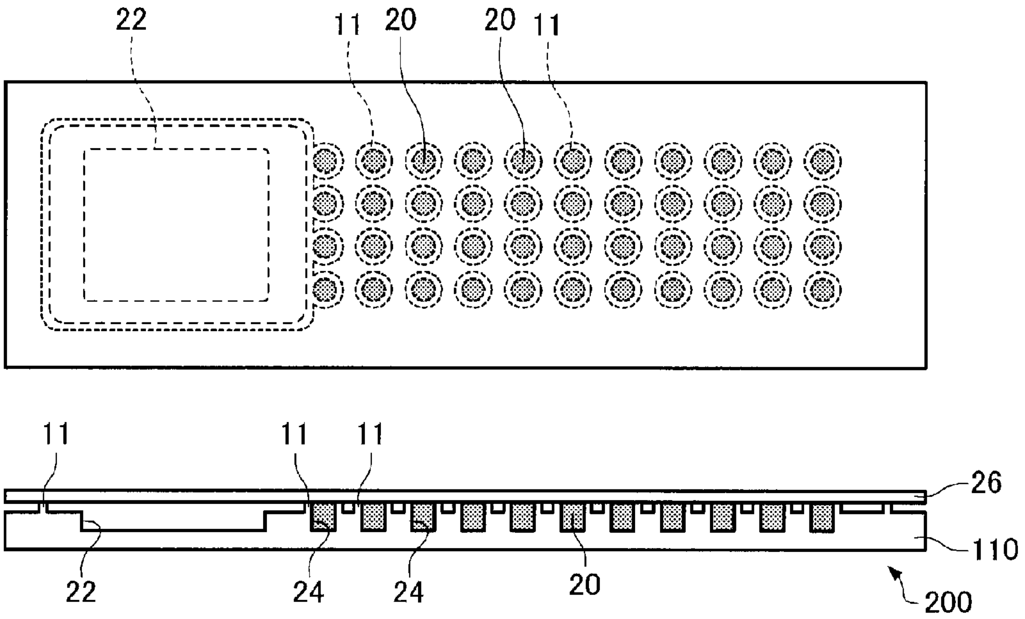
FIG.13
FIG.14
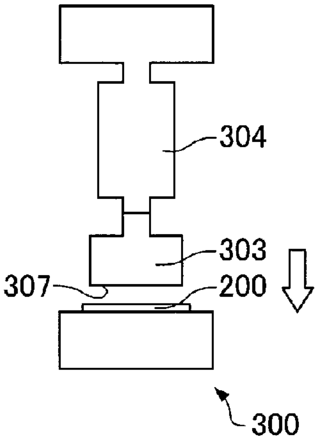

METHOD OF FILLING LIQUID SAMPLE

CROSS-REFERENCE

This application claims priority to Japanese Patent Application No. 2009-282931, filed Dec. 14, 2009, the entirety of which is hereby incorporated by reference.

BACKGROUND

1. Technical Field

The present invention relates to a method of filling a liquid sample.

2. Related Art

A method of performing chemical analysis and chemical synthesis, biotechnology-related analysis, and the like using a microfluidic chip in which a micro flow channel is provided on a glass substrate or the like attracts attention. The microfluidic chip is called micro total analytical system (micro TAS), lab-on-a-chip, or the like. The microfluidic chip has advantages that, for example, necessary amounts of a sample and a reagent are small, a reaction time is short, and an amount of wastes is small compared with an analyzer in the past. Therefore, the microfluidic chip is expected to be used in wide fields such as medical diagnosis, on-site analysis of environment and foods, production of pharmaceuticals, chemicals, and the like (JP-A-2006-509199). Since the necessary amount of the reagent is small in the microfluidic chip, cost of a test decreases. When the necessary amounts of the sample and the reagent are small, since the reaction time is substantially reduced, the test is efficient. In particular, since a necessary amount of a sample such as blood is small, a burden on a patient can be reduced using the microfluidic chip in medical diagnosis.

When an amount of a liquid sample such as a sample or a reagent is small, measurement results tend to fluctuate because dispense accuracy falls and the influence of evaporation of the liquid sample on the amount of the sample is large. In general, dispensing work for the liquid sample is complicated and a work time is long. Since consumables such as a pipette and a chip are consumed in large volume, cost of a test increases. Manual dispensing work for the liquid sample tends to cause mistakes and it is highly likely that undesirable substances are mixed in the liquid sample. According to such a background, there is a demand for a technique for accurately and precisely dispensing a small amount of a liquid sample.

SUMMARY

An advantage of some aspects of the invention is to provide a method of filling a liquid sample that can precisely and accurately dispense the liquid sample at low cost in a simple and easy way while preventing mixing of foreign matters.

According to an aspect of the invention, there is provided a method of filling a liquid sample including:

supplying the liquid sample to a first well of a biochip, the biochip includes:

the first well on a first surface of a substrate, a plurality of second wells that are provided on a first surface of a substrate separated from the first well and include a reagent;

adhering a cover and the substrate on a loop-shaped area that surrounds the first well and the second wells in contact surfaces of the cover and the substrate in a state in which the cover is arranged on the substrate to cover the first well and the second wells;

moving, using centrifugal force, the liquid sample from the first well to the second wells through a space formed between the cover and the substrate in an area further on an inner side than the loop-shaped area by rotating the biochip around a rotation axis in a state in which the biochip is arranged such that a distance from any one of the second wells to the rotation axis is longer than a distance from the first well to the rotation axis; and sealing the first well and the second wells by adhering the cover and the substrate to.

In the aspect of the invention, "the second wells separated from the first well" means that the second wells are provided independently from the first well. For example, this means that the first well and the second wells are not connected by a flow channel. In the invention, "adhere" is a concept including both "welding: adhering contacting portions of plural members by melting" and "bonding: adhering plural members using an adhesive".

In the method of filling a liquid sample, in the moving the liquid sample from the first well to the second wells includes, when the biochip is rotated, the biochip may be arranged such that the first surface is opposed to the rotation axis. The term "opposed" is a concept including not only a case in which the first surface is opposed to the rotation axis in parallel to each other but also a case in which, for example, an angle $\theta_1$ of an acute angle among angles formed by the first surface and the rotation axis is in a range of $0<\theta_1<90$.

In the moving the liquid sample from the first well to the second wells, when the biochip is rotated, the biochip may be arranged such that a distance from the first surface to the rotation axis in the vertical direction with respect to the rotation axis is shorter than a distance from a second surface opposed to the first surface to the rotation axis in the vertical direction with respect to the rotation axis. The term "opposed" is a concept including not only a case in which the first surface is opposed to the second surface in parallel to each other but also a case in which, for example, an angle $\theta_2$ of an acute angle among angles formed by the first surface and the second surface is in a range of $0<\theta_2<90$.

In the method of filling a liquid sample, the cover may have a surface on which an adhesive is arranged. In the adhering the cover and the substrate on the loop-shaped area, the loop-shaped area may be pressed to bond the substrate and the cover on the loop-shaped area.

In the method of filling a liquid sample, the substrate and the cover may have a heat-melting characteristic. In the adhering the cover and the substrate on the loop-shaped area, ultrasound may be irradiated on the loop-shaped area to weld the substrate and the cover on the loop-shaped area.

In the method of filling a liquid sample, ends of the second wells may respectively include projections. In the sealing the first well and the second wells, the projections of the biochip and the cover may be adhered.

In the method of filling a liquid sample, the cover may have an elastically deforming characteristic.

The method of filling a liquid sample includes: supplying the liquid sample to the first well of the biochip; adhering the cover and the substrate on the loop-shaped area surrounding the first well and the second wells in the contact surfaces of the cover and the substrate in the state in which the cover is arranged on the substrate to cover the first well and the second wells; moving, using centrifugal force, the liquid sample from the first well to the second wells through the space formed between the cover and the substrate in the area further on the inner side than the loop-shaped area by rotating the biochip around the rotation axis in the state in which the biochip is arranged such that the distance from any one of the second wells to the rotation axis is longer than the distance from the first well to the rotation axis; and sealing the first well and the second wells by adhering the cover and the substrate. Therefore, it is possible to fill the liquid sample in the second wells in a simple and easy way. Further, it is possible to precisely and accurately dispense the liquid sample at low cost while preventing mixing of foreign matters.

BRIEF DESCRIPTION OF THE DRAWINGS

The invention will be described with reference to the accompanying drawings, wherein like numbers reference like elements.

FIG. 12 is a diagram for explaining a step of welding a biochip and a cover shown in FIG. 10 using an ultrasonic welding device.

FIG. 13 is a diagram for explaining a step of the method of filling a liquid sample according to the second embodiment of the invention.

FIG. 14 is a diagram for explaining a step of welding the biochip and the cover shown in FIG. 11 using the ultrasonic welding device.

DESCRIPTION OF EXEMPLARY EMBODIMENTS

Methods of filling a liquid sample according to embodiments of the invention are specifically explained below.

1. First Embodiment

Method of Filling a Liquid Sample

FIGS. 1 to 3 and FIGS. 5 to 9 are diagrams for explaining steps of a method of filling a liquid sample according to a first embodiment of the invention (in FIGS. 1, 2, 5, 7, and 9, upper diagrams are plan views and lower diagrams are sectional views corresponding to the upper diagrams). FIG. 4 is a perspective view schematically showing a pressing member shown in FIG. 3.

Figure 7:
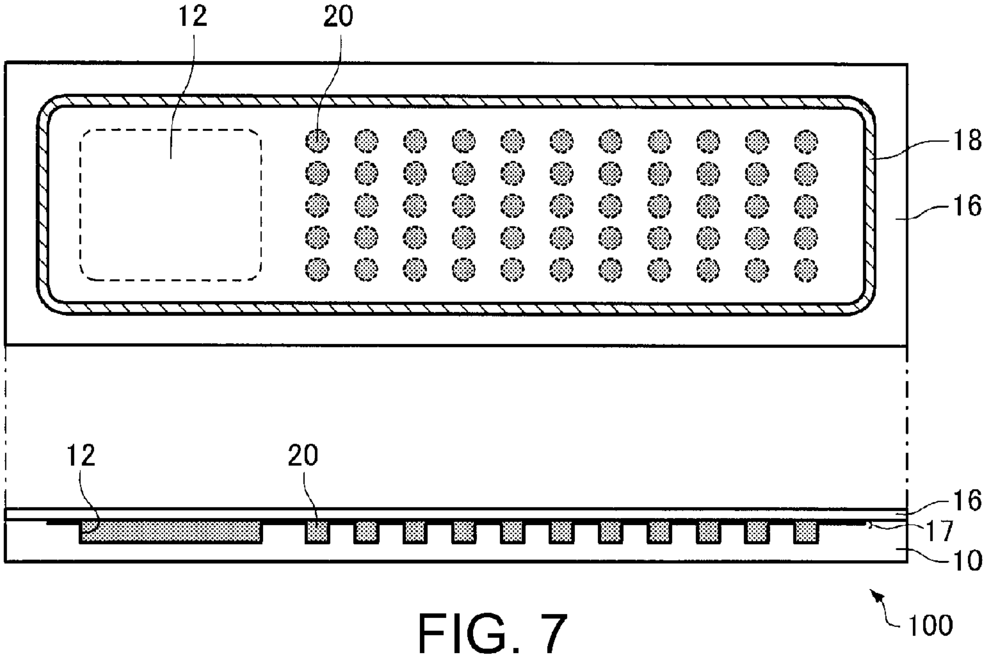
FIG. 7 is a diagram for explaining a step of the method of filling a liquid sample according to the first embodiment of the invention.
Figure 8:
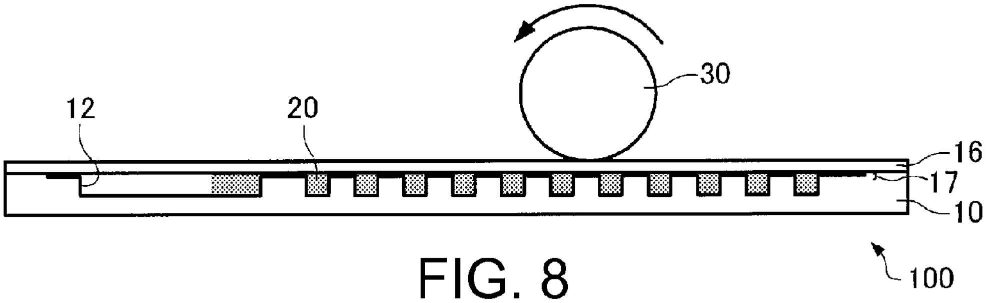
FIG. 8 is a sectional view for explaining a step of the method of filling a liquid sample according to the first embodiment of the invention.
Figure 9:
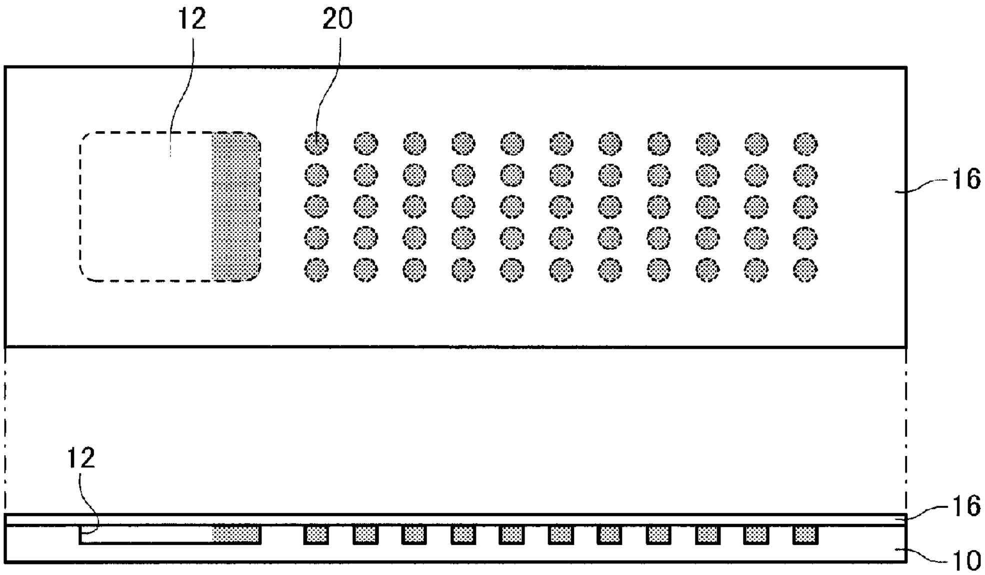
FIG. 9 is a diagram for explaining a step of the method of filling a liquid sample according to the first embodiment of the invention.

The method of filling a liquid sample according to the embodiment of the invention includes: supplying a liquid sample 20 to a first well 12 of a biochip 100 in which the first well 12 and plural second wells 14 separated from the first well 12 and including a reagent are provided on a first surface 10*a* of a substrate 10 (FIGS. 1 and 2); adhering a cover 16 and the substrate 10 on a loop-shaped area 18 (hereinafter also simply referred to as "area") surrounding the first well 12 and the second wells 14 in contact surfaces of the cover 16 and the substrate 10 in a state in which the cover 16 is arranged on the substrate 10 to cover the first well 12 and the second wells 14 (FIGS. 3 to 5); moving, using centrifugal force, the liquid sample 20 from the first well 12 to the second wells 14 through a space 17 formed between the cover 16 and the substrate 10 in an area further on an inner side than the loop-shaped area 18 by rotating the biochip 100 around a rotation axis A in a state in which the biochip 100 is arranged such that a distance from any one of the second wells 14 to the rotation axis A is longer than a distance from the first well 12 to the rotation axis A (FIGS. 6 and 7); and sealing the first well 12 and the second wells 14 by adhering the cover 16 and the biochip 100 to (FIGS. 8 and 9). In the explanation in this embodiment, the biochip 100 is used in order to apply a PCR (Polymerase Chain Reaction) to the liquid sample 20.

1.1. Step of Supplying the Liquid Sample 20

Figure 1:
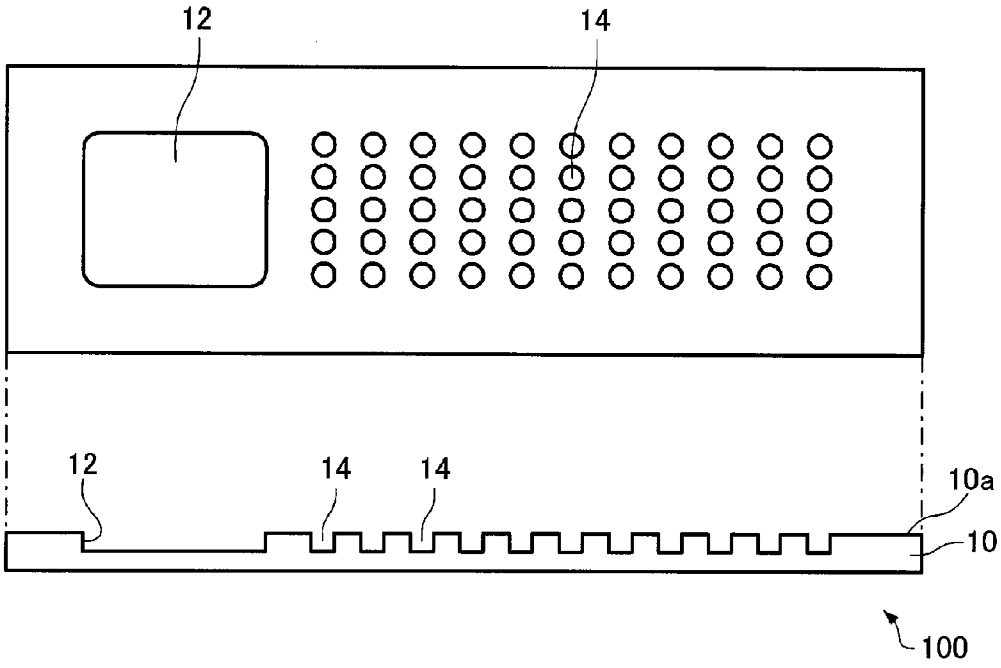
FIG. 1 is a diagram for explaining a step of a method of filling a liquid sample according to a first embodiment of the invention (an upper diagram is a plan view and a lower diagram is a sectional view corresponding to the upper diagram; the same holds true in FIGS. 2, 5, 7, and 9).

As shown in FIG. 1, the biochip 100 used in the method of filling a liquid sample according to this embodiment includes, on the first surface 10*a* of the substrate 10, the first well 12 and the plural second wells 14 separated from the first well 12 and including a reagent. As shown in FIG. 1, the first well 12 and the second wells 14 are recesses provided in the substrate 10. These recesses do not pierce through the substrate 10. In the substrate 10, the first well 12 is provided independently from the plural second wells 14. The first well 12 and the second wells 14 are not connected through a flow channel or the like.

1.1.1. Substrate

In this embodiment, the first surface 10*a* is a surface on which the first well 12 and the second wells 14 are provided in the substrate 10.

Figure 2:
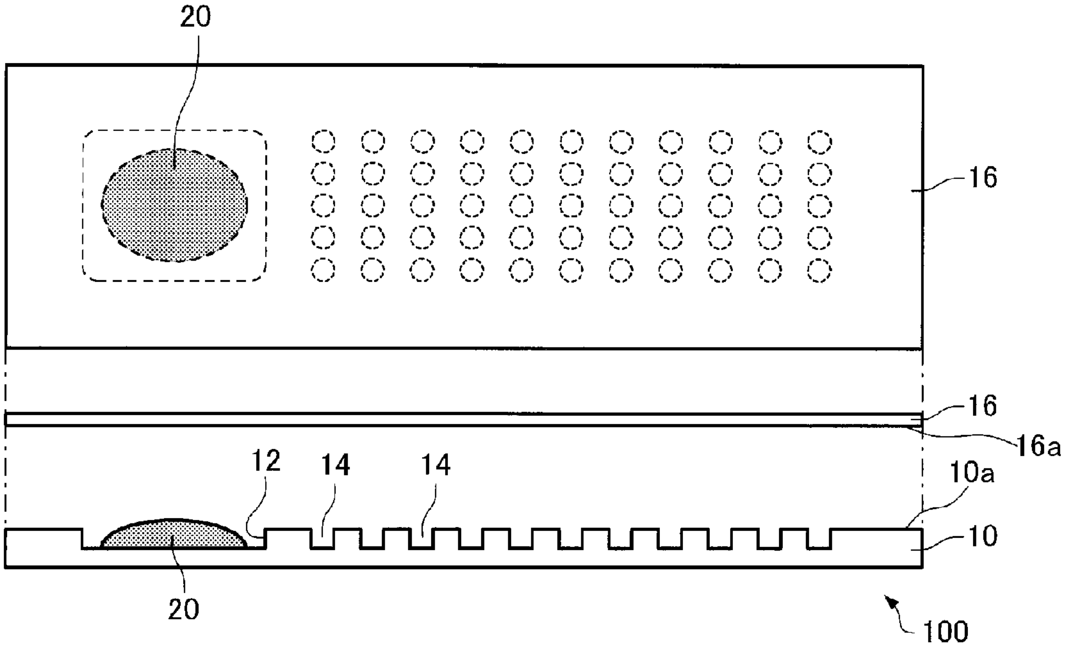
FIG. 2 is a diagram for explaining a step of the method of filling a liquid sample according to the first embodiment of the invention.

The liquid sample 20 is stored in the first well 12 (see FIG. 2). The reagent included in the second wells 14 is, for example, a reagent used for a test for the liquid sample 20. The reagent included in the second wells 14 can be arranged on inner wall surfaces of the second wells 14. After liquid including the reagent is injected into the second wells 14, a solvent in the liquid is dried, whereby the reagent can be arranged on the inner wall surfaces of the second wells 14.

The capacities of the first well 12 and the second wells 14 are respectively determined as appropriate according to conditions such as a test target and a test method. The capacity of the first well 12 is preferably larger than the total capacity of the plural second wells 14 because an amount of the liquid sample 20 sufficient for filling all the plural second wells 14 in a step explained later can be stored.

As shown in FIG. 1, the plural second wells 14 can be arranged to form plural columns and rows. The plural second wells 14 are provided independently from one another and are not connected to one another through a flow channel or the like. For example, the plural second wells 14 are recesses having the same capacity.

When the PCR is performed using the biochip 100, for example, it is also possible that the first well 12 does not include a reagent and the second wells 14 include a reagent containing a primer for amplifying target DNA included in a sample. In this case, in the plural second wells 14 of the biochip 100, primers for respectively amplifying different target DNAs are contained in the reagent and the PCR is performed after the reagent in the second wells 14 are dissolved into the liquid sample 20 in the second wells 14, whereby amplification and analysis of two or more kinds of nucleic acids can be performed at a time using the biochip 100.

A material of the substrate 10 is not specifically limited. However, the substrate 10 is preferably formed of a material that does not damage components included in the liquid sample 20. The substrate 10 can be formed of, for example, an inorganic material (e.g., single-crystal silicon or pyrex (registered trademark) glass) or an organic material (e.g., resin such as polycarbonate). When the substrate 10 is formed of the inorganic material, the first well 12 and the second wells 14 can be formed in the substrate 10 by dry etching employing a photolithography method. When the substrate 10 is formed of resin, the first well 12 and the second wells 14 can be formed on the substrate 10 by, for example, die molding, injection molding, or hot embossing. In the explanation in this embodiment, the substrate 10 is formed of polycarbonate.

1.1.2. Cover 16

A material of the cover 16 is not specifically limited. However, the cover 16 is preferably formed of a material that does not damage the components included in the liquid sample 20. The cover 16 preferably has an elastically deforming characteristic in order to surely generate the space 17 in the step of rotating the biochip 100 explained later (see FIG. 6). Examples of such a cover 16 include resin and rubber.

When the biochip 100 is used for measurement of fluorescent intensity, at least the cover 16 is preferably formed of a transparent and low-autofluorescent material. Both of the substrate 10 and the cover 16 are preferably formed of a transparent and low-autofluorescent material. When the biochip 100 is used for the PCR, the substrate 10 and the cover 16 are preferably a material that can withstand heating in the PCR. Examples of such a material include transparent and low-autofluorescent resin (e.g., polycarbonate).

The cover 16 may have the surface 16*a* on which an adhesive is arranged. The cover 16 having the surface 16*a* on which the adhesive is arranged can be adhered to an object by strongly pressing the surface 16*a* on which the adhesive is arranged against the object (in this embodiment, the first surface 10*a* of the substrate 10). Examples of such a cover 16 include LightCycler 480 Sealing Foil, 04 729 757 001, manufactured by Roche Diagnostics K.K., polyolefin micro plate sealing tape, 9793, manufactured by Sumitomo 3M Limited, and amplification tape 96, 232702, manufactured by Nalge Nunc International Corporation. The surface 16*a* on which the adhesive arranged of the cover 16 may be porous because the surface 16*a* does not show adhesiveness in a non-pressed state and can show adhesiveness when pressed. Alternatively, the adhesive arranged on the surface 16*a* of the cover 16 may be, for example, an adhesive that shows adhesiveness according to application of energy (e.g., an electron beam).

1.1.3. Liquid Sample 20

As shown in FIG. 2, the liquid sample 20 is supplied to the first well 12. For example, the liquid sample 20 can be stored in the first well 12 manually (using a pipette) or mechanically. When the biochip 100 is used for, for example, the PCR, the liquid sample 20 includes a sample that may contain target DNA, a primer for amplifying the target DNA, a fluorescent reagent (e.g., SYBR GREEN (trademark)) for measuring an amount of an amplified product, and a PCR master mix respectively by proper concentrations.

An amount of the liquid sample 20 is appropriately determined according to the capacities of the first well 12 and the second wells 14. The amount of the liquid sample 20 is preferably the same as the total capacity of the plural second wells 14 or larger than the total capacity. The amount of the liquid sample 20 is preferably larger than the total capacity of the plural second wells 14 because the liquid sample 20 can be more surely filled by the plural second wells 14.

The liquid sample 20 is prepared from a sample. When the liquid sample 20 is a target of the PCR, examples of target DNA as a measurement target include DNA extracted from a sample such as blood, urine, saliva, or cerebrospinal liquid or cDNA reverse-transcribed from RNA extracted from the sample.

1.2. Step of Adhering the Cover 16 and the Substrate 10 on the Loop-Shaped Area 18

Figure 3:
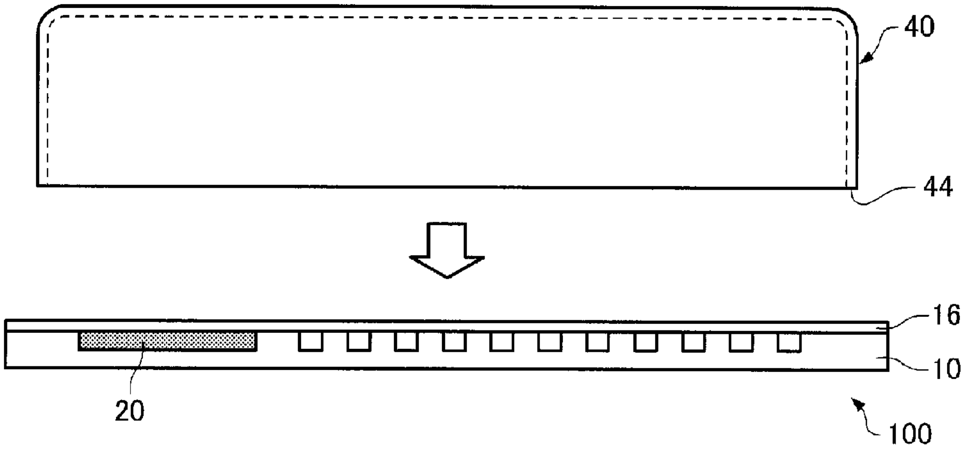
FIG. 3 is a diagram for explaining a step of the method of filling a liquid sample according to the first embodiment of the invention.
Figure 4:
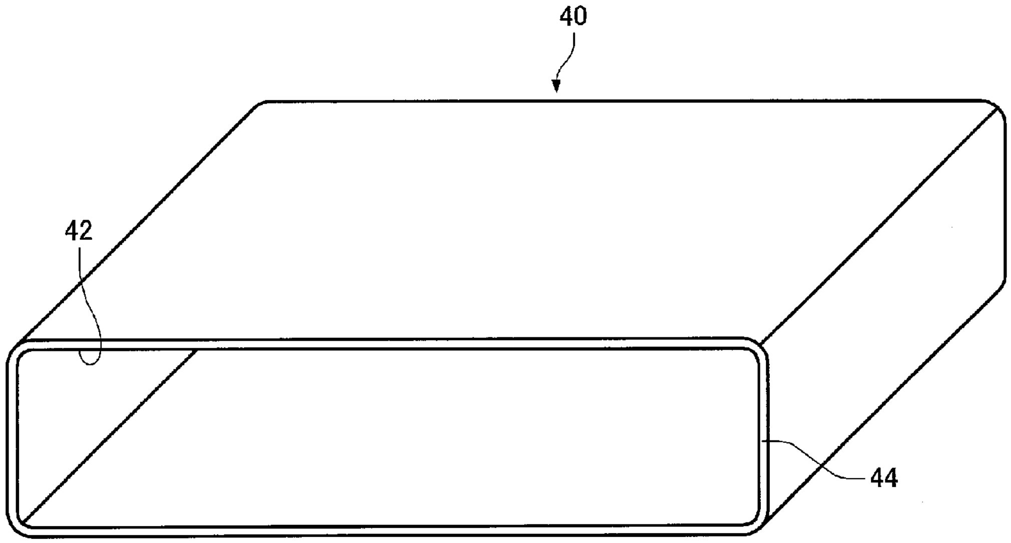
FIG. 4 is a perspective view schematically showing a pressing member shown in FIG. 3.

Subsequently, as shown in FIG. 3, the cover 16 is arranged on the biochip 100 to cover the first well 12 and the second wells 14. In this state, with the substrate 10 and the cover 16 set in contact with each other, the loop-shaped area 18 (an area indicated by hatching in FIG. 5) surrounding the first well 12 and the second wells 14 in the biochip 100 is pressed to adhere (bond) the substrate 10 and the cover 16 in the area 18.

Figure 5:
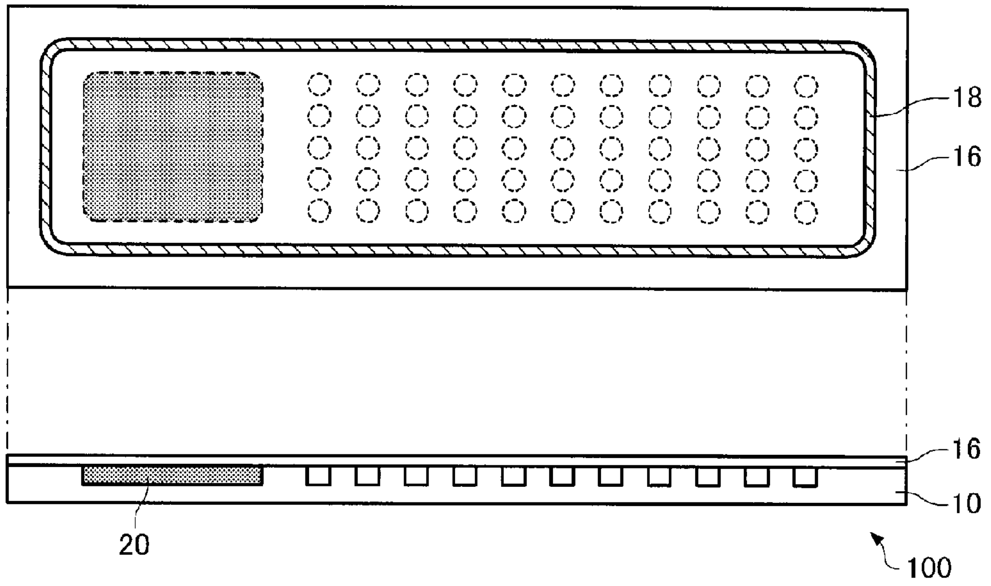
FIG. 5 is a sectional view for explaining a step of the method of filling a liquid sample according to the first embodiment of the invention.

As shown in FIG. 5, the area 18 surrounds the first well 12 and the second wells 14 in a loop shape. The area 18 is formed by arranging the pressing member 40 on the cover 16 and pressing the cover 16 in an arrow direction in FIG. 3 to adhere the substrate 10 and the cover 16.

For example, as shown in FIG. 4, the pressing member 40 has a hollow section 42 and a loop-shaped end face 44 located at an inlet of the hollow section 42. In a state in which the end face 44 of the pressing member 40 is in contact with the cover 16, the pressing member 40 is pressed against the biochip 100. The cover 16 is pressed in the arrow direction in FIG. 3 while being in contact with the end face 44, whereby the cover 16 is bonded to the substrate 10 and the loop-shaped area 18 is formed.

Therefore, in this step, although the substrate 10 and the cover 16 are bonded on the area 18, the substrate 10 and the cover 16 are simply in contact with each other and are not bonded in areas on the inner side and the outer side of the area 18. Specifically, in an area on the inner side than the area 18, the substrate 10 and the cover 16 are not bonded and the cover 16 is simply in contact on the substrate 10. Therefore, the liquid sample 20 enters between the substrate 10 and the cover 16 with centrifugal force, whereby a space is formed in the area further on the inner side than the area 18.

1.3. Step of Moving the Liquid Sample 20 from the First Well 12 to the Second Wells 14

Figure 6:
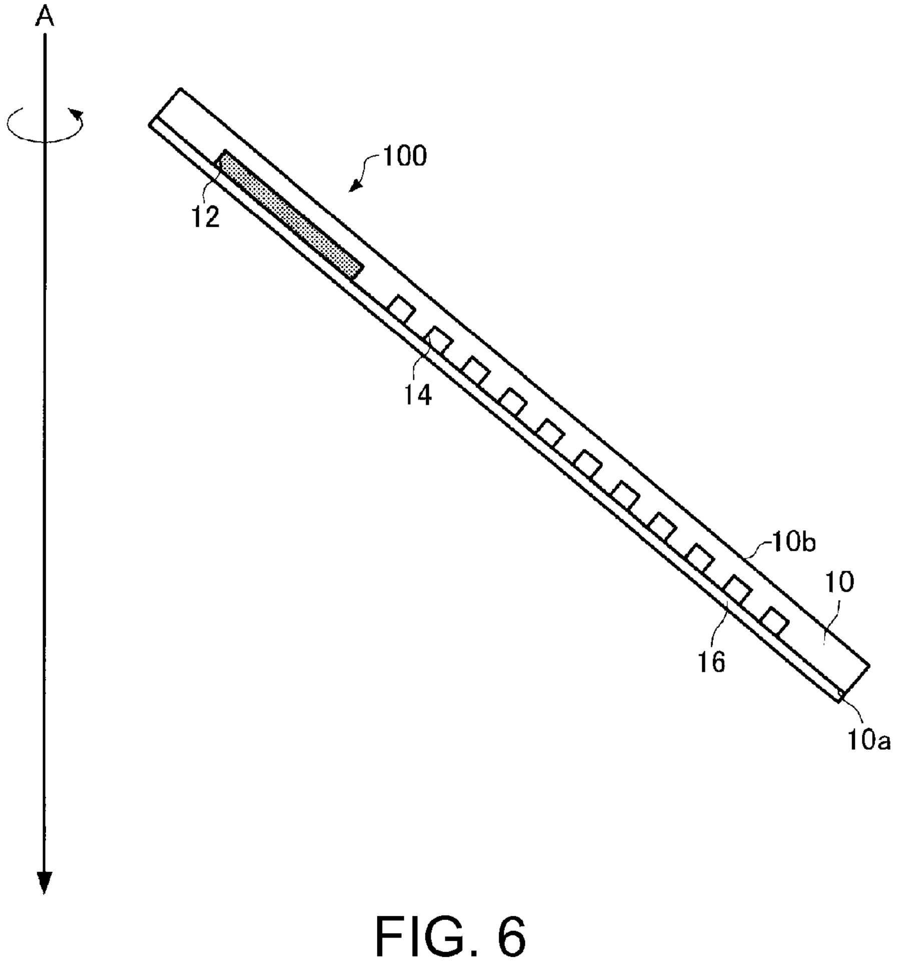
FIG. 6 is a diagram for explaining a step of the method of filling a liquid sample according to the first embodiment of the invention.

Subsequently, as shown in FIG. 6, in a state in which the biochip 100 is arranged such that a distance from any one of the second wells 14 to the rotation axis A is longer than a distance from the first well 12 to the rotation axis A, the biochip 100 is rotated around the rotation axis A, whereby, as shown in FIG. 7, the liquid sample 20 is moved using centrifugal force from the first well 12 to the second wells 14 through the space 17 formed between the cover 16 and the substrate 10 in the area further on the inner side than the loop-shaped area 18. Consequently, the liquid sample 20 is filled in the second wells 14. The distance from the first well 12 (the second wells 14) to the rotation axis A means, as shown in FIG. 6, a distance from an end d1 (d2) of the first well 12 (any one of the second wells 14) to the rotation axis A in a rotating state of the biochip 100. As a device for rotating the biochip 100 around the rotation axis A, for example, a commercially available centrifuge may be used.

In the area further on the inner side than the area 18, since the substrate 10 and the cover 16 are simply in contact with each other, when the biochip 100 is rotated as explained above, the centrifugal force is applied to the liquid sample 20 in a direction away from the rotation axis A on a plane perpendicular to the rotation axis A. Therefore, as shown in FIG. 7, the liquid sample 20 moves from the first well 12 to the second wells 14 through the space 17. On the other hand, since the substrate 10 and the cover 16 are adhered in the area 18, the liquid sample 20 does not leak to the area further on the outer side than the area 18 and remains further on the inner side than the area 18.

More specifically, the cover 16 is elastically deformed by the liquid pressure of the liquid sample 20 and the centrifugal force applied to the cover 16 and distortion occurs in the cover 16. As a result, the space 17 is formed between the cover 16 and the substrate 10. The liquid sample 20 moves from the first well 12 to the second wells 14 through the space 17.

When the biochip 100 is rotated, as shown in FIG. 6, the biochip 100 is arranged such that the first surface 10*a* of the biochip 100 is opposed to the rotation axis A. More specifically, the biochip 100 may be arranged such that a distance in the vertical direction with respect to the rotation axis A from the first surface 10*a* to the rotation axis A is shorter than a distance in the vertical direction with respect to the rotation axis A from a second surface 10*b* opposed to the first surface 10*a* to the rotation axis A.

1.4. Step of Sealing the First Well 12 and the Second Wells 14

Subsequently, the cover 16 is adhered to the substrate 10 to seal the first well 12 and the second wells 14. Consequently, the contact surfaces of the substrate 10 and the cover 16 are entirely bonded (see FIG. 9).

Examples of a method of sealing the first well 12 and the second wells 14 include, as shown in FIG. 8, a method of pressing a roller 30 against the cover 16 while rotating the roller 30 in an arrow direction (a direction from the second wells 14 to the first well 12) on the cover 16. With this method, the liquid sample 20 present in the space 17 between the substrate 10 and the cover 16 moves to the first well 12 and the contact surfaces of the cover 16 and the substrate 10 are bonded. As a result, the first well 12 and the second wells 14 are sealed by the cover 16. The same pressing operation may be performed using a blade (not shown) instead of the roller 30.

1.5. Application of the Biochip 100

With the method of filling a liquid sample according to this embodiment, various kinds of tests can be applied to the biochip 100 in which the liquid sample 20 is filled in the second wells 14. When the PCR is performed using the biochip 100, the PCR can be performed by setting the biochip 100 in which the liquid sample 20 is filled in the second wells 14 in a thermal cycler (not shown) including a flat heat block (not shown).

Since the second wells 14 of the biochip 100 are sealed by the cover 16, evaporation of the liquid sample 20 in temperature cycle processing of the PCR is prevented. Since the cover 16 is formed of a transparent and low-autofluorescent material, quantitative determination of the target DNA (realtime-PCR) may be performed by measuring fluorescent luminance simultaneously with amplification. Analysis of various nucleic acids (DNA and RNA) employing the principle of the PCR including variation of genes such as SNP and methylation of DNA can be performed using the biochip 100.

1.6. Characteristics

The method of filling a liquid sample according to this embodiment includes: supplying the liquid sample 20 to the first well 12 and plural second wells 14 separated from the first well 12 and including a reagent are provided on the first surface 10*a* of the substrate 10; adhering a cover 16 and the substrate 10 on the loop-shaped area 18 surrounding the first well 12 and the second wells 14 in the contact surfaces of the cover 16 and the substrate 10 in the state in which the cover 16 is arranged on the first surface 10*a* to cover the first well 12 and the second wells 14; moving, using centrifugal force, the liquid sample 20 from the first well 12 to the second wells 14 through the space 17 formed between the cover 16 and the substrate 10 in the area further on the inner side than the loop-shaped area 18 by rotating the biochip 100 around the rotation axis A in the state in which the biochip 100 is arranged such that the distance from any one of the second wells 14 to the rotation axis A is longer than the distance from the first well 12 to the rotation axis A; and sealing the first well 12 and the second wells 14 by adhering the cover 16 and the biochip 100. Therefore, with the method of filling a liquid sample according to this embodiment, the liquid sample 20 supplied to the first well 12 can be filled in the second wells 14 in a simple and easy way of a centrifugal action. In filling the liquid sample 20 in the second wells 14, since the cover 16 and the substrate 10 are adhered to each other on the loop-shaped area 18 surrounding the first well 12 and the second wells 14, foreign matters are not mixed externally. Since the liquid sample 20 is moved from the first well 12 to the second wells 14 through the space 17 between the cover 16 and the substrate 10, it is unnecessary to manufacture a flow channel for connecting the first well 12 and the second wells 14 in the substrate 10. Therefore, it is possible to precisely and surely dispense the liquid sample 20 at low cost in a simple and easy way.

With the method of filling a liquid sample according to this embodiment, for example, it is possible to perform dispensing of a very small amount of the liquid sample, which is difficult in manually dispensing the liquid sample using a pipette.

With the method of filling a liquid sample according to this embodiment, the first well 12 and the plural second wells 14 of the biochip 100 are sealed in a state in which each of the plural wells 14 is separated from the first well 12. Therefore, it is possible to prevent backflow of the liquid sample 20 from the second wells 14 to the first well 12. This enables to perform accurate measurement of the liquid sample 20.

With the method of filling a liquid sample according to this embodiment, it is possible to substantially reduce steps for preparation of a reagent and dispensing of the liquid sample. Since it is unnecessary to use expensive equipment such as an automatic dispensing device, it is possible to dispense the liquid sample at low cost.

When both of the substrate 10 and the cover 16 are formed of a transparent and low-autofluorescent material, with the method of filling a liquid sample according to this embodiment, it is possible to perform fluorescent measurement using the biochip 100 in which the liquid sample 20 is filled in the second wells 14. This enables to perform simple and easy measurement.

In the step of moving the liquid sample 20 from the first well 12 to the second wells 14, when the biochip 100 is rotated, as shown in FIG. 6, the biochip 100 may be arranged such that the first surface 10*a* is opposed to the rotation axis A and the distance in the vertical direction with respect to the rotation axis A from any one of the second wells 14 to the rotation axis A is longer than the distance in the vertical direction with respect to the rotation axis A from the first well 12 to the rotation axis A.

An adhesive may be arranged on the cover 16. In the step of adhering the cover 16 and the substrate 10 on the loop-shaped area 18, the loop-shaped area 18 may be pressed to bond the substrate 10 and the cover 16 on the loop-shaped area 18. With this method, since the substrate 10 and the cover 16 are bonded with the adhesive arranged on the cover 16 by pressing the loop-shaped area 18, the substrate 10 and the cover 16 can be adhered simply and easily and at low cost. Since the loop-shaped area 18 is simply pressed in the step of adhering the cover 16 and the substrate 10, heat is not generated, a rise in the temperature of the biochip 100 can be suppressed, and damage to the liquid sample 20 can be reduced.

The cover 16 preferably has an elastically deforming characteristic. With this method, the cover 16 is elastically deformed by the liquid pressure of the liquid sample 20 and the centrifugal force applied to the cover 16 and distortion occurs in the cover 16. As a result, the space 17 can be easily formed between the cover 16 and the substrate 10. The liquid sample 20 can move from the first well 12 to the second wells 14 through the space 17.

In the explanation in this embodiment, the biochip 100 is used for the PCR. However, the biochip 100 obtained by the method of filling a liquid sample according to this embodiment may be used for, for example, tests of viruses, bacteria, protein, low-molecular and high-molecular compounds, cells, particles, colloid, allergy substances such as pollens, poison, hazardous substances, and environmental pollution substances. In the explanation in this embodiment, the second wells 14 of the biochip 100 include the reagent. However, depending on a test content, the second wells 14 may not have to include the reagent.

2. Second Embodiment

Figure 10:
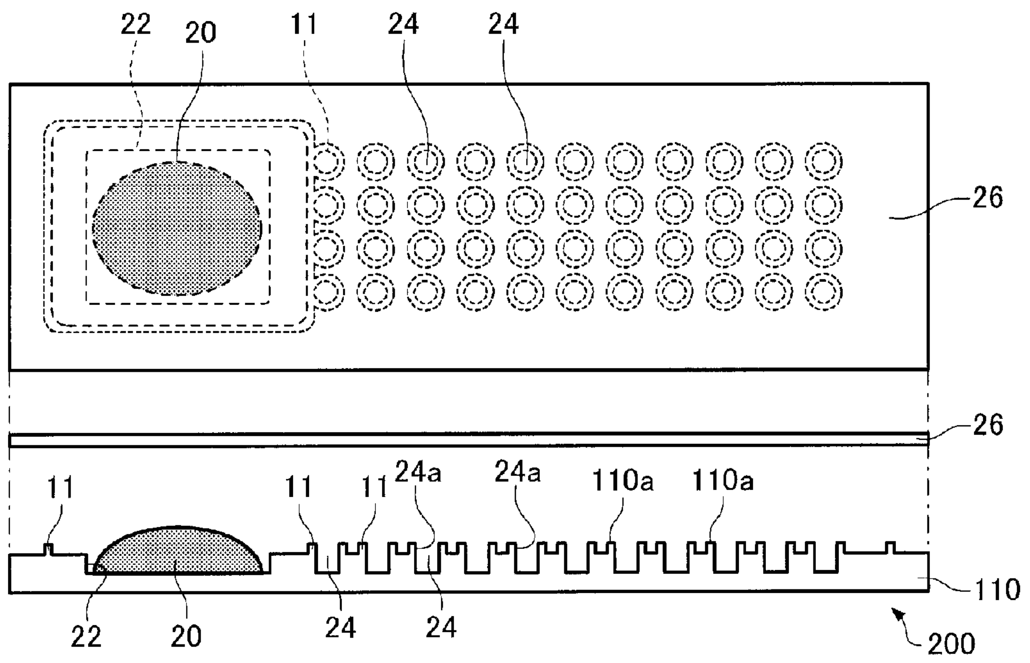
FIG. 10 is a diagram for explaining a step of a method of filling a liquid sample according to a second embodiment of the invention (an upper diagram is a plan view and a lower diagram is a sectional view corresponding to the upper diagram; the same holds true in FIGS. 11 and 13).
Figure 11:
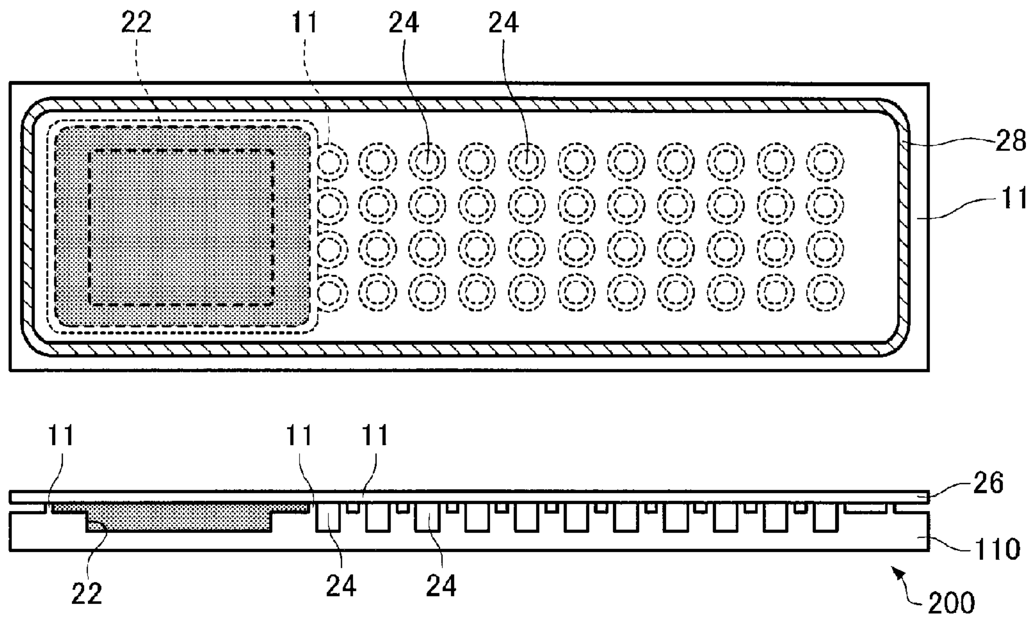
FIG. 11 is a diagram for explaining a step of the method of filling a liquid sample according to the second embodiment of the invention.

FIGS. 10, 11, and 13 are diagrams for explaining steps of a method of filling a liquid sample according to a second embodiment of the invention (in FIGS. 10, 11, and 13, upper diagrams are plan views and lower diagrams are sectional views corresponding to the upper diagrams). FIG. 12 is a diagram for explaining a step of welding the biochip 200 and a cover 26 shown in FIG. 10 using an ultrasonic welding device 300. FIG. 14 is a diagram for explaining a step of adhering (welding) the biochip 200 and the cover 26 shown in FIG. 11 using the ultrasonic welding device 300.

In the method of filling a liquid sample according to this embodiment, the biochip 200 shown in FIG. 10 is used. The biochip 200 is different from the biochip 100 in the first embodiment not including projections 11 in that ends **24*a* of plural second wells 24 are respectively formed by the projections 11. The biochip 200 may be used in the method of filling a liquid sample according to the first embodiment. The biochip 100 used in the method of filling a liquid sample according to the first embodiment may be used in the method of filling a liquid sample according to the second embodiment. A first well 22 and the second wells 24 of the biochip 200 have configurations and functions same as those of the first well 12 and the second wells 14 of the biochip 100** in the first embodiment.

In the method of filling a liquid sample according to this embodiment, components same as those used in the method of filling a liquid sample according to the first embodiment are denoted by the same reference numerals and sigs and detailed explanation of the components is omitted. Among components used in the method of filling a liquid sample according to this embodiment, the components denoted by the reference numerals and signs same as those in the method of filling a liquid sample according to the first embodiment have the same configurations and functions.

The method of filling a liquid sample according to this embodiment is different from the method of filling a liquid sample according to the first embodiment for adhering the substrate 10 and the cover 16 by welding by ultrasound irradiation. Therefore, in the method of filling a liquid sample according to this embodiment, explanation of steps common to those of the method of filling a liquid sample according to the first embodiment is omitted. Steps different from those of the method of filling a liquid sample according to the first embodiment are mainly explained.

Like the cover 16 in the first embodiment, the cover is preferably formed of a transparent and low-autofluorescent material. In the biochip 200, the substrate 110 and the cover 26 have a heat-melting characteristic. The substrate 110 and the cover 26 are preferably formed of the same material because the substrate 110 and the cover 26 can be surely welded. When the biochip 200 is used for the PCR, the substrate 110 and the cover 26 are preferably formed of a material that can withstand heating in the PCR. Examples of such a material include transparent and low-autofluorescent resin (e.g., polycarbonate).

First, the liquid sample 20 is supplied to the first well 22 by a method same as the method of filling a liquid sample according to the first embodiment (see 1.1. above).

Subsequently, as shown in FIG. 10, in a state in which the cover 26 is arranged on the substrate 110 to cover the first well 22 and the second wells 24, as shown in FIG. 11, ultrasound is irradiated on a loop-shaped area (hereinafter simply also referred to as "area") 28 surrounding the first well 22 and the second wells 24 in contact surfaces of the cover 26 and the substrate 110 to weld the substrate 110 and the cover 26 on the area 28. Consequently, the substrate 110 and the cover 26 are adhered in the area 28, while the substrate 110 and the cover 26 are simply in contact with each other in areas further on the inner side and the outer side than the area 28. In other words, in the area further on the inner side than the area 28, there is a space (not shown) in which the liquid sample 20 can move between the substrate 110 and the cover 26.

For the irradiation of the ultrasound, for example, the ultrasonic welding device 300 is used. The ultrasonic welding device 300 converts electric energy into mechanical oscillation energy (ultrasound) with an ultrasonic oscillator 304 and irradiates the ultrasound from a horn 302. The irradiated ultrasound is, for example, 20 kHz.

The ultrasonic welding device 300 includes, as shown in FIG. 12, the ultrasonic oscillator 304 and the horn 302 attached to the ultrasonic oscillator 304. As shown in FIG. 12, the horn 302 has a hollow section 305. The horn 302 has shape same as that of the pressing member 40 shown in FIG. 4. Specifically, the horn 302 has the hollow section 305 and an end face 306. The hollow section 305 and the end face 306 respectively have structures same as those of the hollow section 42 and the end face 44 of the pressing member 40 shown in FIG. 4.

In a state in which the end face 306 of the horn 302 is pressed against the cover 26 on the biochip 200, the horn 302 is pressed against the biochip 200 in an arrow direction in FIG. 12 and ultrasound is intensively emitted from the end face 306. As a result, the ultrasound is intensively irradiated on the area 28 (see FIG. 11) in contact with the end face 306 and frictional heat is generated. The substrate 110 and the cover 26 are melted and adhered (welded) on the area 28.

Subsequently, the liquid sample 20 is moved using centrifugal force from the first well 22 to the second wells 24 through the space (not shown) formed between the cover 26 and the substrate 110 in the area further on the inner side than the loop-shaped area 28 by a method same as the method of filling a liquid sample according to the first embodiment (see 1.3. above).

Subsequently, the ultrasound is irradiated on the entire cover 26, whereby, as shown in FIG. 13, the entire contact surfaces of the substrate 110 and the cover 26 are adhered (welded). Consequently, the first well 22 and the second wells 24 are sealed.

For the irradiation of the ultrasound, for example, the ultrasonic welding device 300 shown in FIG. 14 can be used. The ultrasonic welding device 300 includes, as shown in FIG. 14, the ultrasonic oscillator 304 and a horn 303 attached to the ultrasonic oscillator 304. The horn 303 has a configuration same as that of the horn 302 shown in FIG. 12 except that the hollow section 305 is not provided on the inside.

As shown in FIG. 14, the ultrasound is irradiated on the entire cover 26 by the ultrasonic welding device 300 from above the cover 26 laminated on the biochip 200. In a state in which an end face 307 of the horn 303 is pressed against the cover 26, the horn 303 is pressed against the biochip 200 in an arrow direction in FIG. 14. The ultrasound is irradiated on contact surfaces of the end face 307 of the horn 303 and the cover 26. Consequently, the contact surfaces of the substrate 110 and the cover 26 are adhered (welded). As a result, the first well 22 and the second wells 24 are sealed.

The method of filling a liquid sample according to this embodiment has actions and effects same as those of the method of filling a liquid sample according to the first embodiment. With the method of filling a liquid sample according to this embodiment, since the substrate 110 and the cover 26 are adhered (welded) by the ultrasound irradiation, application of heat on the liquid sample 20 can be suppressed. Therefore, damage to the liquid sample 20 is small. This enables to maintain activity of the reagent included in the second wells 24. Since bonding power of the substrate 110 and the cover 26 is strong, it is possible to surely prevent liquid leakage from the second wells 24.

In the biochip 200 used in the method of filling a liquid sample according to this embodiment, the ends 24*a* of the second wells 24 are respectively formed of the projections 11. Therefore, when the projections 11 and the covers 26 are welded by the ultrasound irradiation, the ultrasound tends to be concentrated on contact surfaces of the projections 11 and the cover 26. This makes it possible to more surely weld the projections 11 and the cover 26. Since the welding by the ultrasound irradiation can suppress a rise in the temperature of the biochip 200, damage to the liquid sample 20 is small.

The embodiments of the invention have been explained. The invention includes configurations substantially the same as the configurations explained in the embodiments (e.g., configurations having the same function, method, and results or configurations having the same object and results). The invention includes configurations in which unessential parts of the configurations explained in the embodiments are replaced. The invention includes configurations that realize actions and effects same as the configurations explained in the embodiments or can attain an object same as that of the embodiments. The invention includes configurations in which a technique in the past is added to the configurations explained in the embodiments.

What is claimed is:

1. A method of filling a liquid sample comprising:

supplying the liquid sample to a first well of a biochip, the biochip includes:

a substrate having a first surface on which the first well is formed, and a plurality of second wells that are formed on the first surface of the substrate, each of the plurality of second wells being, separated from the first well and including, a reagent;

adhering a cover to a loop-shaped area of the substrate that surrounds the first well and the second wells so as to cover the first well and the second wells;

moving the liquid sample from the first well to the second wells through a space between the cover and the substrate by rotating the biochip around a rotation axis in a state in which the biochip is arranged such that a first distance from any one of the second wells to the rotation axis in a direction perpendicular to the rotation axis is longer than a second distance from the first well to the rotation axis in the direction perpendicular to the rotation axis; and sealing the first well and the second wells by adhering the cover to the substrate, wherein in the moving the liquid sample from the first well to the second wells, the biochip is positioned such that the first surface faces the rotation axis when the biochip is rotated around the rotation axis, and in the moving the liquid sample from the first well to the second wells, the biochip is positioned such that a third distance from the first surface to the rotation axis in the direction perpendicular to the rotation axis is shorter than a fourth distance from a second surface of the substrate opposite to the first surface to the rotation axis in the direction perpendicular to the rotation axis when the biochip is rotated around the rotation axis.

2. The method of filling a liquid sample according to claim 1, wherein an adhesive is provided on the cover, and the adhering the cover to the loop-shaped area includes pressing the loop-shaped area to the cover.

3. The method of filling a liquid sample according to claim 1, wherein the substrate and the cover have a heat-melting characteristic, and the adhering the cover to the loop-shaped area includes irradiating ultrasound on the loop-shaped area to melt the substrate and the cover that are located at the loop-shaped area.

4. The method of filling a liquid sample according to claim 1, wherein the first surface of the substrate has projections, and the sealing the first well and the second wells includes adhering the projections and the cover.

5. The method of filling a liquid sample according to claim 1, wherein the cover has an elastically deforming characteristic.

* * * * *